United States Patent [19]
Batz-Sohn et al.

[11] Patent Number: 6,046,349
[45] Date of Patent: Apr. 4, 2000

[54] OLIGOMERIC ORGANOSILICON COMPOUNDS, THEIR USE IN RUBBER MIXTURES AND FOR THE PRODUCTION OF SHAPED ARTICLES

[75] Inventors: Christoph Batz-Sohn, Hanau; Hans-Detlef Luginsland, Köln, both of Germany

[73] Assignee: Degussa-Huels Aktiengesellschaft, Frankfurt, Germany

[21] Appl. No.: 09/343,397

[22] Filed: Jun. 30, 1999

[30] Foreign Application Priority Data

Jul. 1, 1998 [DE] Germany .............. 198 29 390

[51] Int. Cl.$^7$ .................. C07F 7/08; C08K 9/06; C08K 5/24
[52] U.S. Cl. ............. 556/427; 556/426; 152/151; 523/209; 523/213; 523/215; 523/216; 524/155; 524/262; 524/265; 525/102; 525/342; 525/351; 525/352
[58] Field of Search ............... 556/426, 427; 152/151; 523/209, 213, 216; 525/102, 342, 351, 352; 524/155, 262, 265

[56] References Cited

U.S. PATENT DOCUMENTS

| | | | |
|---|---|---|---|
| 3,344,161 | 9/1967 | Moedritzer et al. | 556/427 |
| 5,587,503 | 12/1996 | Heider et al. | 556/427 |
| 5,936,112 | 8/1999 | Gobel et al. | 556/427 |
| 5,977,225 | 11/1999 | Scholl et al. | 524/262 |

FOREIGN PATENT DOCUMENTS

| | | |
|---|---|---|
| 2212239 | 10/1973 | Germany . |
| 3823450 | 2/1990 | Germany . |

*Primary Examiner*—Paul F. Shaver
*Attorney, Agent, or Firm*—Smith, Gambrell & Russell, LLP

[57] ABSTRACT

Oligomeric organosilicon compounds are disclosed of the formula I

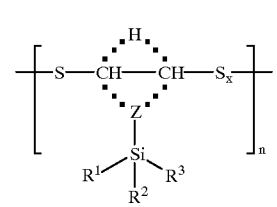

wherein $R^1$, $R^2$, $R^3$ independently of one another denote H, $(C_1-C_4)$alkyl, $(C_1-C_4)$ alkoxy, $(C_1-C_4)$ haloalkoxy, $(C_1-C_4)$haloalkyl, phenyl, aryl or aralkyl and Z denotes an alkylidene radical having 0–6 carbon atoms, x can be a statistical average of 1–6 and n=1–150 and . . . means that z can be bonded either to the one or the other C atom, and the particular free valency is occupied by a hydrogen.

and their use in rubber mixtures and for the production of shaped articles, in particular pneumatic tires.

25 Claims, No Drawings

OLIGOMERIC ORGANOSILICON COMPOUNDS, THEIR USE IN RUBBER MIXTURES AND FOR THE PRODUCTION OF SHAPED ARTICLES

INTRODUCTION AND BACKGROUND

The present invention relates to new oligomeric organosilicon compounds, a process for their preparation and their use in rubber mixtures and for the production of shaped articles.

It is known to employ sulfur-containing organosilicon compounds, such as 3-mercaptopropyltrimethoxysilane or bis-(3-[triethoxysilyl]-propyl) tetrasulfane, as a silane adhesion promoter or reinforcing additive in rubber mixtures with an oxidic filler content, inter alia for treads and other components of car tires (DE 2 141 159, DE 2 212 239, U.S. Pat. Nos. 3,978,103, 4,048, 206).

It is furthermore known that sulfur-containing silane adhesion promoters are employed in the preparation of sealing compositions, casting moulds for metal casting, paint and protective coating films, adhesives, asphalt mixtures and plastics with an oxidic filler content.

Finally, there are possible uses for these compounds in the fixing of active compounds and functional units on inorganic support materials, e.g. in the immobilization of homogenous catalysts and enzymes, in the preparation of fixed bed catalysts and in liquid chromatography.

It is furthermore known that the formation of rubber mixtures with longer-chain polysulfanes, in particular bis-(3-[triethoxysilyl]-propyl) tetrasulfane, chiefly used for adhesion promotion in such rubber mixtures with an oxidic filler content requires particular care during the processing with the rubber, in order to avoid prevulcanization during mixing of the components. The use of organosilanes with shorter polysulfane chains, in particular with disulfane units, which is advantageous in this respect, has been described in respect of the processing and properties of the vulcanization products in EP-A 0732 362 (corresponding to U.S. Pat. No. 5,580,919) and by Panzer (L. Panzer, Am. Chem. Soc., Rubber Div. Meeting 1997). However, a shortening of the polysulfane chains has the effect of an undesirable, lower crosslinking yield between the oxidic filler and the rubber polymer.

DD 262 231 A1 and EP-B1 0 466 066 describe sulfur-rich, oligomeric organoorganooxysilanes with a cycloalkenyl unit which have the disadvantage, however, that their use as a silane adhesive or reinforcing additive leads to vulcanized products with rather average static and dynamic properties, in particular in tensile strength, breaking energy and tensile stress. Moreover, the preparation of this type of compound is complicated and expensive.

It has now been found that the abovementioned disadvantages of the prior art can be substantially avoided by the use of the new oligomeric organosilicon compounds according to the invention as an adhesion promoter or reinforcing additive in rubber mixtures.

SUMMARY OF THE INVENTION

The present invention accordingly relates to new oligomeric organosilicon compounds of the formula I

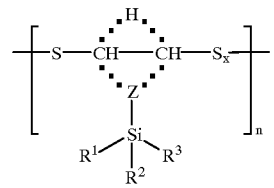

wherein
$R^1$, $R^2$, $R^3$ independently of one another denote H, ($C_1$–$C_4$) alkyl, ($C_1$–$C_4$)alkoxy, ($C_1$–$C_4$)haloalkoxy, ($C_1$–$C_4$)haloalkyl, phenyl, aryl or aralkyl and Z denotes alkylidene having 0–6 carbon atoms, x can be a statistical average of 1–6 and n=1–150 and the designation . . . means that Z can be bonded either to the one or the other C atom, and the particular free valency is occupied by a hydrogen.

Preferred embodiments of the oligomeric organosilicon compounds according to the invention are set forth below together with a description of the process of the invention and products according to the invention.

Thus, organosilicon compounds in which $R^1$, $R^2$ and $R^3$=ethoxy, Z=$CH_2CH_2$ and x=1 are particularly suitable for the use according to the invention.

The oligomeric organosilicon compounds according to the invention as described herein can be cyclic, branched or linear in structure. Preferred compounds are those in which n=20 to 130, particularly preferably n=50 to 100.

The compounds according to the invention can be present both as an individual compound with a defined molecular weight, and as an oligomer mixture with a molecular weight distribution. For process technology reasons, it is as a rule easier to prepare and adopt oligomer mixtures.

DETAILED DESCRIPTION OF THE INVENTION

The preparation of the compounds of the general formula I according to the invention can be carried out easily and in an advantageous manner by a procedure in which compounds of the formula II

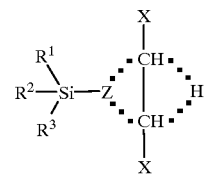

wherein
$R^1$, $R^2$ and $R^3$ and the designation . . . have the abovementioned meaning, X can be halogen,
are reacted with MSH or $M_2S_y$, wherein M is a metal ion and y is a statistical average with a number between 2 and 6 or with $M_2S$ and S, wherein M is a metal ion, optionally in a solvent and optionally at reaction temperatures between 20° C. and 150° C. and optionally under catalytic conditions under pressures between normal pressure or an increased pressure of up to 6 bar, to give compounds of the formula I.

The following procedure is advantageously used for the preparation of the new compounds. A compound of the formula II wherein $R^1$, $R^2$ and $R^3$, X, Z and . . . have the abovementioned meaning is added to a suspension of MSH or $M_2S$ and S, or preciously prepared $M_2S_y$, in a suitable inert solvent or mixtures thereof, such as, for example, in an aromatic solvent, such as chlorobenzene, a halogenated hydrocarbon, such as chloroform, methylene chloride, an ether, such as diisopropyl ether, tert-butyl methyl ether, tetrahydrofuran or diethyl ether, acetonitrile or carboxylic acid esters, for example ethyl acetate, methyl acetate or isopropyl acetate, an alcohol, for example methanol, ethanol, n-propanol, i-propanol, n-butanol, se-butanol or tert-butanol. The mixture is heated for 1 to 24 h, preferably 1 to 8 h under normal pressure or an increased pressure of up to 6 bar, preferably under normal pressure, at temperatures between 20° C. and 150° C., preferably at 35° C. to 80° C., particularly preferably at 55° C. to 65° C., and after the reaction has ended, the precipitate formed is filtered off. After removal of the solvent, the new compounds of the type I as a rule remain as viscous liquids.

Ethanol is used as the particularly preferred solvent. The reactions are advantageously carried out under absolute conditions, i.e. under exclusion of moisture. It is therefore advisable to use predried solvents, such as, for example, analytical grade ethanol.

Ammonium ions, sodium ions or potassium ions are used as preferred metal ions M. The use of the corresponding sodium compound is particularly suitable here.

Various processes of the type described above for sulfidization are known and are described in JP 722 8588, U.S. Pat. Nos. 5,405,985 and 5,466,848. The US patents are relied on and incorporated herein by reference. The reaction can be carried out under catalysis. The catalyst can be employed herein catalytic or stoichiometric amounts.

The compounds of the type II are obtained here starting from the corresponding unsaturated compounds, analogously to DD 262 331A1 or EP-A2 0 350 600. The unsaturated compounds can be obtained as described in EP-A2 0 350 600, relied on herein and incorporated by reference or in an analogous manner.

The compounds of the general type II can also be obtained directly from the corresponding unsaturated compounds in accordance with EP-B1 0 446 066. This patent is expressly relied on, and the content of this patent is intended to be subject matter of the present disclosure and is incorporated herein by reference. The term "alkyl" is to be understood as meaning both "straight-chain" and "branched" alkyl groups. The term "straight-chain alkyl group" is to be understood as meaning, for example, groups such as methyl, ethyl, n-propyl, n-butyl, n-pentyl, n-hexyl, "branched alkyl group" is to be understood as meaning groups such as, for example, isopropyl or tert-butyl. The term "halogen" represents fluorine chlorine, bromine or iodine. The term "alkoxy" represents groups such as, for example, methoxy, ethoxy, propoxy, butoxy, isopropoxy, isobutoxy or pentoxy.

"Aryl" is the context according to the invention is to be understood as meaning $(C_1-C_6)$alkyl-, $(C_1-C_6)$alkoxy-, halogen- or heteroatom-, such as N-, O-, P- or S-substituted phenyls, biphenyls or other benzoid compounds. "Arylalkyl" is to be understood as meaning that the "aryls" described above are bonded to the corresponding silicon atom via a $(C_1-C_6)$alkyl chain, which in turn can be $(C_1-C_4)$ alkyl- or halogen-substituted. If "aryl" has heteroatom, such as O or S, the $(C_1-C_6)$alkyl chain can then also establish a bond with the silicon atom via the heteroatom.

When defining the substituents, such as e.g. $(C_1-C_4)$ alkoxy, the number in the index designates the number of all the carbon atoms in the radical.

The preparation of the oligomeric organosilicon compounds according to the invention is shown by way of example in examples 1 and 2.

The oligomeric organosilicon compounds thus obtained in a simple manner are surprisingly particularly suitable for use in rubber mixtures.

Rubber mixtures which comprise the organosilicon compounds according to the invention as an adhesion promoter or reinforcing additive and shaped articles resulting after a vulcanization step, in particular pneumatic tires or tire treads, have, after carrying out the processes according to the invention, a low rolling resistance with simultaneously good adhesion in the wet and high abrasion resistance.

The present invention therefore provides rubber mixtures comprising rubber, filler, in particular also precipitated silica and optionally further rubber auxiliary substances, and at least one organosilicon compound according to the invention which is built up from the structure set forth in claim 1 and which is employed in amounts of 0.1 to 15 wt. %, particularly preferably 5–10 wt. %, based on the amount of the oxidic filler employed.

When the organosilicon compounds claimed are used in rubber mixtures, advantages are found in the static and dynamic data of the vulcanization products compared with the mixtures according to the prior art (cf. table 4). This manifests itself in particular in a higher tensile strength, breaking energy and a higher 300% stress value. Moreover, the mixture with the organosilicon compounds claimed shows a reduced build up of heat (Goodrich flexometer test), which indicates positive hysteresis properties.

The organosilicon compounds according to the invention and the fillers are preferably added at material temperatures of 100 to 200° C. but they can also be added later at lower temperatures (40 to 100° C.), e.g. together with further rubber auxiliary substances.

The organosilicon compounds according to the invention can be added to the mixing process either in the pure form or in a form absorbed on an inert organic or inorganic support. Preferred support materials are silicas, naturally occurring or synthetic silicates, aluminum oxide or carbon blacks.

Possible fillers for the rubber mixtures according to the invention are:

Carbon blacks: the carbon blacks to be used here are prepared by the flame black, furnace black or gas black process and have BET surface areas of 20 to 200 $m^2/g$. The carbon blacks can optionally also contain heteroatoms, such as e.g. Si.

highly disperse silicas, prepared e.g. by precipitation of solutions of silicates or flame hydrolysis of silicon halides with specific surface areas of 5 to 1000, preferably 20 to 400 $m^2/g$ (BET surface area) and with primary particle sizes of 10 to 400 nm. The silicas can optionally also be present as mixed oxides with other metal oxides, such as Al, Mg, Ca, Ba, Zn and titanium oxides.

Synthetic silicates, such as aluminum silicate, alkaline earth metal silicates, such as magnesium silicate or calcium silicate, with BET surface areas of 20 to 400 $m^2/g$ and primary particle diameters of 10 to 400 nm.

Naturally occurring silicates, such as kaolin and other naturally occurring silicas.

Glass fibers and glass fiber products (mats, strands) or glass microbeads.

Preferably, carbon blacks with BET surface areas of 20 to 400 $m^2/g$ or highly disperse silicas, prepared by precipitation of solutions of silicates, with BET surface areas of 20 to 400 $m^2/g$ are employed, in amounts of 5 to 150 parts by wt., in each case based on 100 parts of rubber.

The fillers mentioned can be employed by themselves or as a mixture. In a particularly preferred embodiment of the process, 10 to 150 parts by wt. of light-coloured fillers, optionally together with 0 to 100 parts by wt. of carbon black, and 0.1 to 15 parts by wt., preferably 5 to 10 parts by wt. of a compound of the formula (I), in each case based on 100 parts by wt. of the filler employed, are employed for the preparation of the mixtures.

In addition to naturally occurring rubber, synthetic rubbers are also suitable for the preparation of the rubber mixtures according to the invention. Preferred synthetic rubbers are described, for example, in W. Hofmann, Kautschuktechnologie [Rubber Technology], Genter Verlag, Stuttgart 1980. They include, inter alia, polybutadiene (BR)
polyisoprene (IR)
styrene/butadiene copolymers with styrene contents of 1 to 60, preferably 2 to 50 wt. % (SBR)
isobutylene/isoprene copolymers (IIR)
butadiene/acrylonitrile copolymers with acrylonitrile contents of 5 to 60, preferably 10 to 50 wt. % (NBR)
partly hydrogenated or completely hydrogenated NBR rubber (HNBR)
ethylene/propylene/diene copolymers (EPDM)and mixtures of these rubbers. Anionically polymerized L-SBR rubbers with a glass transition temperature above −50° C. and mixtures thereof with diene rubbers are of particular interest for the production of motor vehicle tires.

The rubber vulcanization products according to the invention can comprise further rubber auxiliary products, such as reaction accelerators, antioxidants, heat stabilizers, light stabilizers, anti-oxonants, processing auxiliaries, plasticizers, tackifiers, blowing agents, dyestuffs, waxes, extenders, organic acids, retardants, metal oxides and activators, such as triethanolamine, polyethylene glycol, hexanetriol, which are known to the rubber industry.

The rubber auxiliaries are employed in conventional amounts, which depend, inter alia, on the intended use. Conventional amounts are e.g. amounts of 0.1 to 50 wt. %, based on the rubber. The oligomeric silanes can be used by themselves as crosslinking agents. As a rule, the addition of further crosslinking agents is advisable. Sulfur or peroxides can be employed as further known crosslinking agents. The rubber mixtures according to the invention can furthermore comprise vulcanization accelerators. Examples of suitable vulcanization accelerators are mercaptobenzothiazoles, sulfenamides, guanidines, thiurams, dithiocarbamates, thioureas and thiocarbonates. The vulcanization accelerators and sulfur or peroxides are employed in amounts of 0.1 to 10 wt. %, preferably 0.1 to 5 wt. %, based on the rubber.

The vulcanization of the rubber mixtures according to the invention can be carried out at temperatures of 100 to 200° C., preferably 130 to 180° C., optionally under a pressure of 10 to 200 bar. The mixing of the rubbers with the filler, optionally rubber auxiliary substances and the silanes according to the invention can be carried out in conventional mixing units, such as rolls, internal mixers and mixing extruders. The rubber vulcanization products according to the invention are suitable for the production of shaped articles, e.g. for the production of pneumatic tires, tire treads, cable sheathings, hoses, drive belts, conveyor belts, roller coverings, tires, shoe soles, sealing rings and damping elements.

The preparation of the rubber mixtures and of the vulcanization products is described by way of example in examples 3 and 5. The superior properties of the compounds according to the invention compared with the prior art (comparison examples 3 and 5) are shown with the aid of example 4, which uses an oligomeric organosilicon compound according to the invention as the adhesion promoter.

EXAMPLES 1–2

Preparation of the Organosilanepolysulfanes

Example 1

1. 86 g $Na_2S$ and 35.0 g sulfur are suspended in 1.50 l ethanol and the mixture is head to 60° C. 289 g (1.00 mol) 3, 4-dichlorobutyltriethoxysilane are then added dropwise and the mixture is headed under reflux for 5 h. Thereafter, it is allowed to cool and the NaCl formed is filtered off. After removal of the solvent by distillation, 225 g (80% of theory) of the compound of the formula I where $R^1$=EtO), $R^2$=EtO, $R^3$=EtO, Z═$CH_2$—$CH_2$, x=1 remain.

Analysis values:
Calculated C 42.52 H 7.85 S 22.7
Found C 42.70 H 7.92 S 22.52

Example 2

2. 86 g $Na_2S$ and 71.0 g sulfur are suspended in 1.50 l ethanol and the mixture is heated to 60° C. 289 g (1.00 mol) 3, 4-dichlorobutyl-triethoxysilane are then added dropwise and the mixture is heated under reflux for 5 h. Thereafter, it is allowed to cool and the NaCl formed is filtered off. After removal of the solvent by distillation, 245 g (78% of theory) of the compound of the formula I where $R^1$=EtO, $R^2$=EtO, $R^3$=EtO, Z═$CH_2CH_2$, x=1.45 remain.

Analysis values:
Calculated C 40.45 H 7.47 S 26.46
Found C 40.70 H 7.56 S 26.3

Examples 3–5

Preparation of the Rubber Mixtures and Vulcanization Products

General Procedure Instructions

The recipe used for the rubber mixtures is given in the following table 1. The unit phr here means parts by weight per 100 parts of the crude rubber employed.

TABLE 1

| Substance | Amount [phr] |
| --- | --- |
| 1st stage | |
| Buna VSL 5025-1 | 96.0 |
| Buna CB 24 | 30.0 |
| Ultrasil VN3 | 80.0 |
| ZnO | 3.0 |
| Stearic acid | 2.0 |
| Naftolene ZD | 10.0 |
| Vulkanox 4020 | 1.5 |
| Protector G35P | 1.0 |
| TESPT | 6.4 |
| 2nd stage | |
| Batch stage 1 | |
| 3rd stage | |
| Batch stage 2 | |
| Vulkacit D | 2.0 |
| Vulkacit CZ | 1.5 |
| Sulfur | 1.5 |

The polymer VSL 5025-1 is an SBR copolymer from Bayer AG polymerized in solution and having a styrene content of 25 wt. % and a butadiene content of 75 wt. %. Of the butadiene 73% is linked as 1, 2, 10% as cis-1, 4 and 17% as trans-1,4. The copolymer comprises 37.5 phr oil and has a Mooney viscosity (ML 1+4/100° C.) of 50±5.

The polymer Buna CB 24 is a cis-1, 4-polybutadiene (Neodym type) from Bayer AG with a cis-1, 4 content of 97%, a trans-1, 4 content of 2%, a 1,2 content of 1% and a Mooney viscosity of between 39 and 49.

The silica VN3 from Degussa-Hüls AG has a BET surface area of 175 m²/g. Bis-(3-[triethoxysilyl]-propyl) tetrasulfane (TESPT) is marketed under the trade name SI 69 by Degussa-Hüls AG.

Naftolene ZD from Chemetall was used as the aromatic oil; Vulkanox 4020 is PPD from Bayer AG, and Protrector G35P is an anti-ozonant wax from HB-Fuller GmbH. Vulkacit D (DPG) and Vulkacit CZ (CBS) are commercial products from Bayer AG.

The rubber mixture is prepared in three stages in an internal mixer in accordance with the following tabular list:

TABLE 2

Stage 1

Settings

| | |
|---|---|
| Mixing unit | Werner & Pfleiderer |
| Friction | 1:1.11 |
| Speed | 70 min$^{-1}$ |
| Plunger pressure | 5.5 bar |
| Empty volume | 1.6 L |
| Filling level | 0.55 |
| Flow temp. | 70° C. |

Mixing operation

| | |
|---|---|
| 0 to 1 min | Buna VSL 5025-1 + Buna CB 24 |
| 1 to 3 min | ½ Ultrasil VN3, ZnO, stearic acid, Naftolen ZD, silane |
| 3 to 4 min | ½ Ultrasil VN3, Vulkanox 4020, Protector G35P |
| 4 min | clean |
| 4 to 5 min | mix |
| 5 min | clean |
| 5 to 6 min | mix and deliver |
| Batch temp | 140–150° C. |
| Storage | 24 h at room temperature |

Stage 2

Settings

| | |
|---|---|
| Mixing unit | as in stage 1 except: |
| Speed | 80 min$^{-1}$ |
| Filling level | 0.53 |
| Flow temp. | 90° C. |

Mixing operation

| | |
|---|---|
| 0 to 2 min | break up batch stage 1 |
| 2 to 5 min | maintain batch temperature 150° C. by varying speed |
| 5 min | deliver |
| Batch temp. | 150–155° C. |
| Storage | 4 h at room temperature |

Stage 3

Settings

| | |
|---|---|
| Mixing unit | as in stage 1 except |
| Speed | 40 min$^{-1}$ |
| Filling level | 0.51 |
| Flow temp. | 50° C. |

Mixing operation

| | |
|---|---|
| 0 to 2 min | Batch stage 2 + Vulkacit CZ + Vulkacit D + sulfur |
| 2 min | deliver and form skin on laboratory roll mill (diameter 200 mm, length 450 mm, flow temperature 50° C.) Homogenization: cut in 3* left, 3* right and fold over, and turn over 8* for a narrow roll nip (1 mm) and 3* for a wide roll nip (3.5 mm) and then draw out a skin |
| Batch temp | 90–100° C. |

The general process for the preparation of rubber mixtures and vulcanization products thereof is described in the following: "Rubber Technology Handbook", W. Hofmann, Hanser Verlag 1994. The vulcanization time for the test specimens is 60 minutes at 165° C.

The rubber testing is carried out in accordance with the test methods described in table 3.

TABLE 3

| Pysical testing | Standard/Conditions |
|---|---|
| ML 1 + 4, 100° C. | DIN 53523/3 ISO 667 |
| Vulkameter test, 165° C. | DIN 53529/3, ISO 6502 |
| Tensile test on ring, 23° C. Tensile strength Tensile values Elongation at break | DIN 53504, ISO 37 |
| Shore A hardness, 23° C. | DIN 53 505 |
| Ball rebound, 0 and 60° C. | ASTM D 5308 |
| Viscoelastic properties, 0 and 60° C., 16 Hz, 50N preliminary force and 25N amplitude force Complex modulus E*, Loss factor tan δ | DIN 53 513, ISO 2856 |
| Goodrich flexometer, 25 min at 23° C. and 0.175 inch stroke | DIN 53 533, ASTM D 623 A |
| DIN abrasion, 10N force | DIN 53 516 |
| Dispersion | ISO-DIS 11345 |

Examples 3, 4 and 5

Examples 3 (comparison example), 4 and 5 (comparison example) are carried out in accordance with the general procedure instructions.

In a modification to comparison example 3, instead of bis(3-[triethoxysilyl]-propyl) tetrasilane (TESPT) the organosilicon compound from example 1 is added to the mixture. Example 5 is also a comparison example, and instead of TESPT contains the oligomeric organosilane according to EP-BL 0 466 066. The following rubber data for the crude mixture and vulcanization product result (table 4):

TABLE 4

| Feature: | Unit | 3 | 4 | 5 |
|---|---|---|---|---|
| Crude mixture results | | | | |
| ML (1 + 4), 100° C. 3$^{rd}$ stage | [MU] | 54 | 57 | 53 |
| MDR 165° C. | | | | |
| Dmax-Dmin | [dNm] | 17.56 | 20.70 | 19.47 |
| t 10% | [min] | 1.99 | 1.66 | 2.02 |
| t 90% | [min] | 15.69 | 42.19 | 31.89 |
| Vulcanizer results | | | | |
| Tensile test on ring | | | | |
| Tensile strength | [MPa] | 12.4 | 14.3 | 12.8 |
| Tensile value 100% | [MPa] | 2.0 | 2.1 | 1.9 |
| Tensile value 300% | [MPa] | 10.1 | 10.8 | 9.4 |
| Elongation at break | [%] | 340 | 360 | 370 |
| Breaking energy | [J] | 55.2 | 67.7 | 62.3 |
| Shore A hardness (23° C.) | [SH] | 64 | 65 | 66 |
| Ball rebound (0° C.) | [%] | 11.1 | 11.6 | 11.5 |
| Ball rebound (60° C.) | [%] | 60.4 | 59.2 | 56.4 |
| DIN abrasion | [mm$^3$] | 70 | 69 | 87 |
| Viscoelastic testing | | | | |
| Dyn. extension modulus E* (0° C.) | [MPa] | 26.1 | 24.3 | 25.6 |
| Dyn. extension modulus E* (60° C.) | [MPa] | 9.4 | 9.4 | 9.4 |
| Loss factor tan δ (0° C.) | [-] | 0.484 | 0.487 | 0.491 |
| Loss factor tan δ (60° C.) | [-] | 0.116 | 0.121 | 0.129 |

TABLE 4-continued

| Feature: | Unit | 3 | 4 | 5 |
|---|---|---|---|---|
| Goodrich flexometer | | | | |
| Contact temperature | [° C.] | 46 | 42 | 43 |
| Puncture temperature | [° C.] | 88 | 83 | 85 |
| Permanent set | [%] | 2.5 | 1.7 | 1.4 |
| Dispersion | [-]- | 8 | 8 | 8 |

Further variations and modifications will be apparent to those skilled in the art from the foregoing and are intended to be encompassed by the claims appended hereto.

German priority document 198 29 390.9 is relied on and incorporated herein by reference.

We claim:

1. An oligomeric organosilicon compound of the formula I

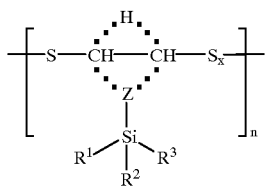

wherein $R^1$, $R^2$, $R^3$ independently of one another denote H, ($C_1$–$C_4$) alkyl, ($C_1$–$C_4$) alkoxy, ($C_1$–$C_4$) haloalkoxy, ($C_1$–$C_4$) haloalkyl, phenyl, aryl or aralkyl and Z denotes alkylidene having 0–60 carbon atoms, x is a statistical average of 1–6 and n=1–150 and the designation . . . means that Z can be bonded either to the one or the other C atom, and the particular free valency is occupied by a hydrogen.

2. The oligomeric organosilicon compound according to claim 1, wherein $R^1$, $R^2$, $R^3$=ethoxy, Z=$CH_2CH_2$ and x=1.

3. The oligomeric organosilicon compound according to claim 1 wherein n=20 to 130.

4. The oligomeric organosilicon compound according to claim 2 wherein n=20 to 130.

5. The oligomeric organosilicon compound according to claim 1 wherein n=50 to 100.

6. The oligomeric organosilicon compound according to claim 2 wherein n=50 to 100.

7. A process for the preparation of the oligomeric organosilicon compound according to claim 1 comprising reacting a compound of the formula II

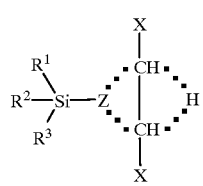

wherein $R^1$, $R^2$, $R^3$ Z and . . . have the given meaning and X is halogen, with MSH or $M_2S_y$, wherein M is a metal ion and y is a statistical average with a number between 2 and 6, or with $M_2S$ and S, wherein M is a metal ion, optionally in a solvent and optionally at reaction temperatures between 20° C. and 150° C. and optionally under catalytic conditions under pressures between normal pressure or an increased pressure of up to 6 bar, to yield a compound of the formula I.

8. The process according to claim 7, wherein the metal ion is an ammonium ion, sodium ion or potassium ion.

9. The oligomeric organosilicon compound obtainable by a process according to claim 7.

10. The oligomeric organosilicon compound obtainable by a process according to claim 8.

11. A rubber mixture comprising an oligomeric organosilicon compound mixed with a rubber according to claim 1.

12. A rubber mixture according to claim 11, wherein the organosilicon compound is present in an amount of 0.1 to 15 wt. %, based on the amount of filler employed.

13. A rubber mixture according to claim 11, wherein the organosilicon compound is present in an amount of 5 to 10 wt. %, based on the amount of filler employed.

14. A rubber mixture according to claim 11 comprising a synthetic rubber and silica as the filler.

15. A process for the preparation of a rubber mixture comprising mixing a rubber, at least one filler and an oligomeric organosilicon compound according to claim 1 together to form a rubber mixture.

16. A shaped article obtainable from a rubber mixture according to claim 11.

17. The shaped article according to claim 16, which is a pneumatic tire.

18. The shaped article according to claim 16, which is a tire tread.

19. A process for using a rubber mixture for the production of a shaped article, comprising selecting a rubber formulation meeting the desired characteristics for the shaped article, mixing said rubber with the compound of claim 1 to form a rubber mixture and molding said mixture into the desired shape.

20. A process for forming a shaped article of rubber comprising selecting the rubber mixture of claim 11, shaping it into the desired confirmation and vulcanizing said rubber to form the desired article.

21. An oligomeric organosilicon compound according to claim 1 deposited on an inert inorganic or organic support.

22. The oligomeric organosilicon compound according to claim 1 deposited on carbon black or silica as a support.

23. The rubber mixture according to claim 11 wherein said rubber is a naturally occurring rubber or synthetic rubber.

24. The rubber mixture according to claim 11 which is unvulcanized.

25. The rubber mixture according to claim 11 which is vulcanized.

* * * * *